US010527618B2

(12) United States Patent
Shinohara et al.

(10) Patent No.: US 10,527,618 B2
(45) **Date of Patent: *Jan. 7, 2020**

(54) SAMPLE PROCESSING METHOD FOR INFLUENZA VIRUS IMMUNOASSAY, AND IMMUNOASSAY METHOD

(71) Applicant: DENKA SEIKEN CO., LTD., Tokyo (JP)

(72) Inventors: Yuki Shinohara, Gosen (JP); Takashi Miyazawa, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/917,632

(22) PCT Filed: Sep. 10, 2014

(86) PCT No.: PCT/JP2014/073971

§ 371 (c)(1),
(2) Date: Mar. 9, 2016

(87) PCT Pub. No.: WO2015/037635

PCT Pub. Date: Mar. 19, 2015

(65) Prior Publication Data

US 2016/0223540 A1 Aug. 4, 2016

(30) Foreign Application Priority Data

Sep. 10, 2013 (JP) ................................ 2013-187355

(51) Int. Cl.
*G01N 33/569* (2006.01)

(52) U.S. Cl.
CPC ... *G01N 33/56983* (2013.01); *G01N 2333/11* (2013.01)

(58) Field of Classification Search
None
See application file for complete search history.

(56) References Cited

U.S. PATENT DOCUMENTS 4,810,630 A * 3/1989 Craig ............... G01N 33/54393 435/188
2015/0031052 A1 1/2015 Kano et al.
2015/0079581 A1* 3/2015 Iwamoto .......... G01N 33/56983 435/5

FOREIGN PATENT DOCUMENTS

| | | | |
|---|---|---|---|
| EP | 2602619 | A1 | 6/2013 |
| JP | 2006-84351 | A | 3/2006 |
| JP | 2008-14752 | A | 1/2008 |
| JP | 2012-73270 | A | 4/2012 |
| JP | 2013-140035 | A | 7/2013 |

OTHER PUBLICATIONS

Bucher et al. (Journal of Clinical Microbiology, 1991, p. 2484-2488).*
Extended European Search Report dated May 4, 2017, in European Patent Application No. 14843481.4.
Bucher et al., "M Protein (M1) of influenza Virus: Antigenic Analysis and Intracellular Localization with Monoclonal Antibodies," Journal of Virology, vol. 63, No. 9, Sep. 1989, pp. 3622-3633.

* cited by examiner

*Primary Examiner* — Agnieszka Boesen
(74) *Attorney, Agent, or Firm* — Birch, Stewart, Kolasch & Birch, LLP

(57) ABSTRACT

Means for enabling an immunoassay with a sufficient sensitivity in an immunoassay for measuring influenza virus in a sample using influenza virus M1 protein as an antigen is provided. A sample processing method in an immunoassay for influenza virus, which method comprises, in an immunoassay for influenza virus using an antibody which undergoes antigen-antibody reaction with influenza virus matrix 1 protein, or an antigen-binding fragment thereof, bringing a sample containing influenza virus into contact with a sample processing liquid containing a surfactant having at least one group selected from the group consisting of palmityl, stearyl, and oleyl, is provided.

3 Claims, No Drawings

SAMPLE PROCESSING METHOD FOR INFLUENZA VIRUS IMMUNOASSAY, AND IMMUNOASSAY METHOD

TECHNICAL FIELD

The present invention relates to a sample processing method in an immunoassay for influenza virus using influenza virus matrix 1 protein (which may hereinafter be referred to as "M1") as an antigen, and an immunoassay method.

BACKGROUND ART

Methods such as isolation culture, PCR, ELISA, EIA, Western blotting, and immunochromatography, are generally known as methods for detecting influenza virus. Since influenza virus is a seasonal pathogen, many patients with influenza visit hospitals in a short period, and a large number of viral tests are carried out in the short period at actual clinical sites. Therefore, immunochromatography is recently becoming common at medical sites because of its rapidness and simplicity.

As common methods of immunochromatography, methods using membranes such as nitrocellulose membranes are known. In these methods, a ligand that specifically binds to the substance to be detected is immobilized on a membrane, and this ligand captures, through the substance to be detected, a complex containing a labeled substance in which a ligand that specifically binds to the substance to be detected is labeled, thereby allowing an assay on the presence or absence of the substance to be detected in the sample. The labeled substance is generally a ligand which specifically binds to the substance to be detected and which is labeled with an enzyme such as alkaline phosphatase, with a colloidal metal such as colloidal gold, or with a colored polystyrene particle prepared by staining with a dye. In particular, a colloidal gold particle or a colored polystyrene particle is used in many cases.

Most chromatographic methods for detection of influenza virus which are currently commercially available are based on methods for assaying the presence or absence of influenza virus in a sample by detection of nucleoprotein (NP). However, these methods cannot necessarily be said to have sufficient detection sensitivity, and detection of influenza virus by these methods is difficult in cases where the sample is derived from a patient within 6 hours after occurrence of fever. Therefore, further improvement of the detection sensitivity has been demanded.

Well-known examples of proteins constituting influenza virus include HA protein, NA protein, nucleoprotein (NP), and matrix proteins 1 and 2 (M1 and M2). The protein present in the largest number in each influenza virus particle is M1 protein. The amount of M1 protein is reported to be about 3 times larger than that of NP protein (Non-patent Document 1).

Surfactant treatment of samples to be subjected to immunoassays is known as described in Patent Document 1 and Patent Document 2.

PRIOR ART DOCUMENTS

Patent Documents

[Patent Document 1] JP 4976068 B
[Patent Document 2] JP 2012-73270 A

Non-Patent Document

[Non-patent Document 1] Standard Microbiology 10th Edition, Igaku-Shoin Ltd.

SUMMARY OF THE INVENTION

Problems to be Solved by the Invention

The present inventors attempted to construct an immunochromatography method for detecting influenza virus M1 protein. However, in immunochromatography for detection of M1 protein wherein a sample extraction method was carried out using a sample processing liquid containing a conventionally used surfactant, Triton X100 (trade name) or Brij35 (trade name), as described in the paragraph 0031 of Patent Document 1 or the paragraphs 0026 to 0027 of Patent Document 2, the sensitivity was evidently low, so that the method was impractical (see Example 4 and Table 5 shown below).

An object of the present invention is to provide means which enables an immunoassay with a sufficient sensitivity in an immunoassay for measuring influenza virus in a sample using influenza virus M1 protein as an antigen

Means for Solving the Problems

As a result of intensive study, the present inventors discovered that, by bringing a sample containing influenza virus into contact with a particular surfactant, the measurement sensitivity of an immunoassay for influenza M1 protein can be increased, thereby completing the present invention.

That is, the present invention provides a sample processing method in an immunoassay for influenza virus, the method comprising, in an immunoassay for influenza virus using an antibody which undergoes antigen-antibody reaction with influenza virus matrix 1 protein, or an antigen-binding fragment thereof, bringing a sample containing influenza virus into contact with a sample processing liquid containing a surfactant having at least one group selected from the group consisting of palmityl, stearyl, and oleyl. The present invention also provides an immunoassay method for influenza virus, the method comprising subjecting a sample processed by the above-described method of the present invention to an immunoassay method using an antibody which undergoes antigen-antibody reaction with influenza virus matrix 1 protein, or an antigen-binding fragment thereof, to measure influenza virus in the sample.

Effect of the Invention

By the present invention, in an immunoassay for measuring influenza virus in a sample using influenza virus M1 protein as an antigen, the sensitivity of the immunoassay can be increased.

MODE FOR CARRYING OUT THE INVENTION (Sample)

The sample to which the present invention is applicable is not limited as long as the presence of influenza virus in the sample is suspected. The sample is preferably a nasopharynx-derived sample such as a nasal swab, nasal aspirate, nasal blow, throat swab, or saliva (hereinafter referred to as nasopharynx-derived sample). A nasal swab or a nasal aspirate is especially preferred.

(Sample Processing Liquid)

As described above, in the method of the present invention, the sample is brought into contact with a surfactant. This is usually carried out by treating a sample processing liquid containing the surfactant with the sample. The sample processing liquid usually contains the surfactant in a buffer. Examples of the buffer include, but are not limited to, MES, HEPES, TES, ADA, ACES, bis-Tris, Tris, TES, CAPS, borate buffer, phosphate buffer, and citrate buffer. The surfactant is a surfactant having at least one group selected from the group consisting of palmityl, stearyl, and oleyl. These alkyl groups may be either linear or branched. The surfactant is preferably a nonionic surfactant in which at least one of the aliphatic groups is bound to a polyoxyethylene chain. The chain length of the polyoxyethylene chain is not limited. The degree of polymerization of oxyethylene units is usually 5 to 40, preferably 10 to 20. Preferred examples of the surfactant having a polyoxyethylene chain include polyoxyethylene oleyl ether, polyoxyethylene stearyl ether, and polyoxyethylene cetyl ether. These surfactants may be used individually, or two or more of the surfactants may be used in combination. The final concentration of the surfactant in the sample processing liquid (in cases where a plurality of the surfactants are contained, the total final concentration of the surfactants) is preferably 0.005 (w/v) % to 8 (w/v) %, more preferably 0.5 (w/v) % to 4 (w/v) %. The surfactants may be used individually, or two or more of the surfactants may be used in combination.

In the method of the present invention, the surfactant is preferably brought into contact with the sample in the presence of a chloride. Therefore, the sample processing liquid preferably further contains a chloride. Preferred examples of the chloride include alkali metal chlorides such as lithium chloride, sodium chloride, and potassium chloride. The final concentration of the chloride in the sample processing liquid is preferably 0.05 M to 1.5 M, especially preferably 0.1 M to 1.0 M. The chlorides may be used individually, or two or more of the chlorides may be used in combination.

(Other Components Contained in Sample Processing Liquid)

The sample processing liquid may also contain one or more of basic amino acids such as arginine; nonionic surfactants such as polyoxyethylene octyl phenyl ether (e.g., Triton (registered trademark) X-100); non-specific reaction inhibitors such as BSA; stabilizers and preservatives such as sucrose; and antiseptics such as ProClin (registered trademark). The sample processing liquid may also contain one or more reagents to be used in the process of adjusting the pH of the buffer, such as sodium hydroxide or hydrogen chloride.

(Sample Processing Method)

The sample processing method of the present invention is carried out by bringing a sample such as a nasopharynx-derived sample into contact with the sample processing liquid of the present invention. For example, in cases where the sample is a nasal aspirate, a cotton swab or the like is soaked in the nasal aspirate, and the cotton swab soaked with the sample is placed in the sample processing liquid of the present invention to dissolve the sample into the sample processing liquid. By this, the sample can be extracted. In cases where the sample is a nasal swab sample, the nasal cavity is wiped with a cotton swab, and the cotton swab soaked with the sample is placed in the sample processing liquid of the present invention to dissolve the sample into the sample processing liquid. By this, the sample can be extracted. This operation can be carried out at room temperature. The amount of the sample processing liquid in which the cotton swab is soaked is not limited as long as the whole cotton portion in the cotton swab can be soaked in the sample processing liquid. The amount of the sample processing liquid may usually be 0.05 mL to 5 mL.

(Immunoassay)

The sample processed as described above is subjected to an immunoassay method using an antibody which undergoes antigen-antibody reaction with influenza virus M1 protein, or an antigen-binding fragment thereof, to measure influenza virus in the sample. This immunoassay is described below.

(Virus to be Measured)

The virus to be measured in the immunoassay of the present invention is influenza virus such as influenza A virus or influenza B virus. The "measurement" in the present invention includes any of detection, quantification, and semi-quantification.

(Antibody)

The immunoassay of the present invention uses influenza virus M1 protein as an antigen. Therefore, the immunoassay uses an antibody which undergoes antigen-antibody reaction with influenza virus M1 protein, or an antigen-binding fragment thereof.

For the measurement of influenza A virus, an antibody which undergoes antigen-antibody reaction with influenza A virus M1 (which may hereinafter be referred to as A-M1), or an antigen-binding fragment thereof, is used. A-M1 is a protein constituted by 252 amino acid residues, and its signal due to antigen-antibody reaction can be specifically detected at a molecular weight of 20 to 35 kD when the antibody is used for detection by Western blotting. The term "specific" in the present description means that, in a liquid system containing a mixture of proteins and the antibody, the antibody does not cause antigen-antibody reaction with the protein components other than A-M1 at a detectable level, or, even in cases where the antibody causes a certain binding reaction or association reaction with a protein component other than A-M1, the reaction is evidently weaker than the antigen-antibody reaction between the antibody and A-M1. Amino acid sequences of A-M1 are known, and described in, for example, GenBank: ACD37490. The anti-A-M1 antibody may be either a monoclonal antibody or a polyclonal antibody. From the viewpoint of reproducibility, a monoclonal antibody is preferred. The anti-A-M1 monoclonal antibody can be easily prepared by immunizing an animal with A-M1 or a partial peptide thereof, and then carrying out the method of Kohler et al. (Kohler et al., Nature, vol. 256, p. 495-497 (1975)), which is a conventional method. The class of the monoclonal antibody is not limited to IgG, and may also be IgM or IgY.

An antigen-binding fragment prepared by isolating only the antigen-binding site may also be used for the immunoassay. That is, fragments having specific antigen-binding capacity (antigen-binding fragments), such as Fab, Fab', $F(ab')_2$, and single-chain antibodies (scFv) prepared by known methods may also be used.

For measurement of influenza B virus, an antibody which undergoes antigen-antibody reaction with influenza B virus M1 (which may hereinafter be referred to as B-M1), or an antigen-binding fragment thereof, is used. B-M1 is a protein constituted by 248 amino acid residues, and its signal due to antigen-antibody reaction can be specifically detected at a molecular weight of 20 to 35 kD when the antibody is used for detection by Western blotting. Amino acid sequences of B-M1 are known, and described in, for example, GenBank: AEN79424. Similarly to the cases of type A, an antigen-binding fragment may be used also for influenza B virus.

The immunoassay per se is well known, and any of sandwich methods, agglutination methods, competition methods, and various well-known immunoassays may be employed. Among these, sandwich methods are preferred. Among sandwich methods, immunochromatography or ELISA is preferred. Immunochromatography is especially preferred from the viewpoint of simplicity of the operation. The sandwich method is carried out using two kinds of monoclonal antibodies capable of binding to the antigen, influenza virus M1 protein, at the same time, or antigen-binding fragments thereof. The immunochromatography, which is a preferred sandwich method, is described below. Immunochromatography per se is well known and widely used. A well-known method for immunochromatography may be used also in the present invention.

(Immunochromatography for Detection of Substance to be Detected)

The method of immunochromatographic detection of the substance to be detected in the present invention (immunochromatography) is not limited as long as it is an immunological detection method using an antibody against the substance which is to be detected (which may hereinafter be referred to as an antibody against the substance to be detected). The method is preferably a sandwich method using an antibody against the substance to be detected and a labeled antibody against the substance to be detected. The antibody against the substance to be detected may be either a polyclonal antibody or a monoclonal antibody. A monoclonal antibody is preferred. The immunochromatography is carried out by bringing a substance to be detected, extracted by the sample processing method described above, into contact with a strip or the like on which the antibody against the substance to be detected is immobilized. Needless to say, the immunochromatography in the present invention can be used for both qualitative detection and quantitative measurement.

(Labeling Substance)

Preferred examples of the labeling substance with which the antibody is labeled include colloidal gold particles, colloidal platinum particles, colored latex particles, and magnetic particles. Colored latex particles are especially preferred.

The colored latex particles can be prepared by, for example, preparing polystyrene particles by soap-free polymerization without using an emulsifier according to the method described in [0022] of JP 6-306108 A, and then carrying out the method described in [0025] to [0035] of the same document. Alternatively, colored particles which are commercially available from, for example, Seradyn Inc. or Magsphere Inc. may be used.

Cases where colored latex particles are used as the labeling substance are described below in detail.

(Method for Immobilization of Labeled Antibody)

The immobilization of the antibody on the colored latex is usually carried out by chemical bonding. The antibody concentration in this process is preferably 1 mg/mL to 5 mg/mL, and the buffer and the pH are preferably 20 mM MES buffer (pH 5.5 to 6.5) or 50 mM borate buffer (pH 8 to 9), more preferably 20 mM MES buffer (pH 6.5). The areas on the colored latex particles where the antibody is not bound are preferably blocked by binding of BSA or the like. The thus prepared colored latex-labeled antibody is stored as a dispersion in a preservation reagent which inhibits denaturation. Examples of the denaturation inhibitor include proteins such as BSA; glycerin; and sugars.

(Solid Phase)

Examples of the material of the solid phase include polyethylene; polyethylene terephthalate; nylons; glasses; polysaccharides such as cellulose and cellulose derivatives; and ceramics. Preferred specific examples of the material of the solid phase include glass fiber filter papers, cellulose filter papers, and the like commercially available from, for example, Millipore, Toyo Roshi Kaisha, Ltd., Whatman, and Rydell; polystyrene plates; glass fiber membranes; nylon membranes; and nitrocellulose membranes. Nitrocellulose membranes are especially preferred. Cases where a nitrocellulose membrane is used as the material of the solid phase are described below.

(Immobilization of Capture Antibody on Solid Phase)

The capture antibody for detection of the complex of the antigen as the substance to be detected (for example, influenza virus) and the labeled antibody may be immobilized on a nitrocellulose membrane by a generally well-known method. For example, in cases of a lateral-flow type, an apparatus having a mechanism by which a liquid containing the capture antibody can be discharged from a nozzle at a constant rate while the apparatus horizontally moves is used to linearly apply the capture antibody liquid to a cellulose membrane. The concentration of the antibody in this process is preferably 0.1 mg/mL to 5 mg/mL, more preferably 0.5 mg/mL to 2 mg/mL. Normally, the antibody liquid can be prepared using a predetermined buffer. Examples of the type of the buffer include normally used buffers such as phosphate buffer, Tris buffer, and Good's buffer. The buffer preferably has a pH within the range of 6.0 to 9.5, more preferably 6.5 to 8.5, still more preferably 7.0 to 8.0. The buffer may also contain one or more of salts such as NaCl; stabilizers and preservatives such as sucrose; and antiseptics such as ProClin (registered trademark). Examples of the salts include not only those to be included for adjustment of the ionic strength, such as NaCl, but also those to be present during the process of adjusting the pH of the buffer, such as sodium hydroxide.

After the immobilization of the antibody on the nitrocellulose membrane, the membrane may be coated with a normally used blocking agent in the form of a solution or a vapor, to carry out blocking.

By appropriately selecting the pore size of the nitrocellulose membrane, the flow rate of the immune complex of the colored-latex-labeled antibody and the antigen as the substance to be detected (for example, influenza virus) in the membrane can be controlled. Since, by controlling this flow rate, the amount of the labeled antibody bound to the antibody immobilized on the membrane can be controlled, it is preferred to select a membrane having an appropriate pore size. Hi Flow Plus HF180, manufactured by Millipore, or the like is preferably used.

(Immunochromatography Reagent, and Immunochromatography Reagent Kit)

The sample processing liquid of the present invention may be used together with a conventional immunochromatography reagent(s), or these may be used in combination as an immunochromatography reagent or an immunochromatography reagent kit.

The "immunochromatography reagent" includes one or more of reagent components necessary for the measurement by immunochromatography, and members such as test strips.

Essentially, in the present invention, it can be said that the presence of the particular surfactant mentioned above, or the presence of the particular salt in addition to the particular surfactant, in the immunochromatographic system for detection of influenza virus is important for highly sensitive detection. In view of this, Examples are described below for cases where the method for processing influenza virus is carried out with a sample processing liquid prepared in a liquid state. However, the present invention is not limited to the Examples, and any mode in which an immunochromatographic system for detection of influenza virus contains the particular surfactant mentioned above, or the particular salt in addition to the particular surfactant, is within the scope of the present invention.

EXAMPLES

1. Preparation of Anti-Influenza B Virus M1 Monoclonal Antibodies

BALB/c mice were immunized with an influenza B virus antigen, and kept for a certain period. From each mouse, the spleen was removed, and fusion with mouse myeloma cells (P3×63) was carried out by the method of Kohler et al. (Kohler et al., Nature, vol. 256, p. 495-497 (1975)). The resulting fused cells (hybridomas) were kept in an incubator at 37° C. The cells were then purified (into monoclonal cells) while the antibody activity in the supernatant was checked by ELISA using a plate on which an influenza B virus M1 antigen is immobilized. Each of two cell lines obtained was intraperitoneally administered to pristane-treated BALB/c mice. About two weeks later, antibody-containing ascites was collected. From the ascites obtained, IgG was purified by affinity chromatography using a protein A column. By this, two kinds of purified anti-influenza B virus M1 antibodies were obtained.

2. Immobilization of Anti-Influenza B Virus Antibody on Nitrocellulose Membrane

A liquid prepared by diluting the purified anti-influenza B virus M1 antibody with purified water to 1.0 mg/mL was linearly applied to a predetermined position of a nitrocellulose membrane lined with a PET film. The membrane was then dried at 45° C. for 30 minutes to obtain a membrane on which the anti-influenza B virus M1 antibody is immobilized (hereinafter referred to as "antibody-immobilized membrane".

3. Immobilization of Anti-Influenza B Virus Antibody on Colored Polystyrene Particles The other purified anti-influenza B virus M1 antibody, which was not used for the immobilization on the nitrocellulose membrane, was diluted with purified water to 1.0 mg/mL, and colored polystyrene particles were added to the resulting dilution at 0.1%. The resulting mixture was stirred, and carbodiimide was then added thereto at 1%, followed by further stirring the mixture. The supernatant was removed by centrifugation, and the precipitate was resuspended in 50 mM Tris (pH 9.0) supplemented with 3% BSA, to obtain colored polystyrene particles to which the anti-influenza B virus M1 antibody is bound.

4. Application/Drying of Colored Polystyrene Particles to which Anti-Influenza B Virus M1 Antibody is Bound A predetermined amount, 1.0 μg, of the colored polystyrene particles to which the anti-influenza B virus M1 antibody is bound obtained in 3 were applied to a glass-fiber non-woven fabric, and the non-woven fabric was then dried at 45° C. for 30 minutes.

5. Lamination with Antibody-Immobilized Membrane, Dry Pad, and Other Members

The antibody-immobilized membrane and the dry pad prepared in 2 and 4 were laminated with other members (backing sheet, absorption zone, and sample pad), and the resulting laminate was cut into a piece with a width of 5 mm, to provide an influenza B virus test piece.

6. Preparation of Anti-Influenza A Virus M1 Monoclonal Antibody

BALB/c mice were immunized with an influenza A virus antigen, and kept for a certain period. From each mouse, the spleen was removed, and fusion with mouse myeloma cells (P3×63) was carried out by the method of Kohler et al. (Kohler et al., Nature, vol. 256, p. 495-497 (1975)). The resulting fused cells (hybridomas) were kept in an incubator at 37° C. The cells were then purified (into monoclonal cells) while the antibody activity in the supernatant was checked by ELISA using a plate on which an influenza A virus M1 antigen is immobilized. Each of two cell lines obtained was intraperitoneally administered to pristane-treated BALB/c mice. About two weeks later, antibody-containing ascites was collected. From the ascites obtained, IgG was purified by affinity chromatography using a protein A column. By this, two kinds of purified anti-influenza A virus M1 antibodies were obtained.

7. Immobilization of Anti-Influenza A Virus Antibody on Nitrocellulose Membrane

A liquid prepared by diluting the purified anti-influenza A virus M1 antibody with purified water to 1.0 mg/mL was linearly applied to a predetermined position of a nitrocellulose membrane lined with a PET film. The membrane was then dried at 45° C. for 30 minutes to obtain a membrane on which the anti-influenza A virus M1 antibody is immobilized (hereinafter referred to as "antibody-immobilized membrane".

8. Immobilization of Anti-Influenza A Virus Antibody on Colored Polystyrene Particles The other purified anti-influenza B virus M1 antibody, which was not used for the immobilization on the nitrocellulose membrane, was diluted with purified water to 1.0 mg/mL, and colored polystyrene particles were added to the resulting dilution at 0.1%. The resulting mixture was stirred, and carbodiimide was then added thereto at 1%, followed by further stirring the mixture. The supernatant was removed by centrifugation, and the precipitate was resuspended in 50 mM Tris (pH 9.0) supplemented with 3% BSA, to obtain colored polystyrene particles to which the anti-influenza A virus M1 antibody is bound.

9. Application/Drying of Colored Polystyrene Particles to which Anti-Influenza A Virus M1 Antibody is Bound A predetermined amount, 1.0 μg, of the colored polystyrene particles to which the anti-influenza A virus M1 antibody is bound obtained in 8 were applied to a glass-fiber non-woven fabric, and the non-woven fabric was then dried at 45° C. for 30 minutes.

10. Lamination with Antibody-Immobilized Membrane, Dry Pad, and Other Members

The antibody-immobilized membrane and the dry pad prepared in 7 and 9 were laminated with other members, backing sheet, absorption zone, and sample pad, and the resulting laminate was cut into a piece with a width of 5 mm, to provide an influenza A virus test piece.

Example 1. Selection of Optimal Type of Surfactant

In order to search for an optimal surfactant for immunochromatography for detecting influenza A and B virus M1 proteins, performances of surfactants were compared. First, sample processing liquids each containing one of the surfactants shown in Table 1 at a concentration of 1 (w/v) %, and also containing 10 mM MES (pH 7.0) and 3% BSA as other components, were prepared. The sample processing liquid containing No. 4, polyoxyethylene octyl phenyl ether, in Table 1, corresponds to a conventional sample processing method. Table 1 also shows the carbon number of the polyoxyethylene (POE) chain of each surfactant used. For the tests for influenza A virus, Nos. 1 to 7 in Table 1 were used. For the tests for influenza B virus, only Nos. 2 to 4 in Table 1 were used.

Subsequently, 30 μL of inactivated influenza A virus or inactivated influenza B virus was added to 400 μL of each of the sample processing liquids prepared, and each resulting mixture was mixed. To the sample pad portion of the influenza A or B virus test piece, 50 μL of the mixture was added dropwise, and visual judgment was carried out 10 minutes later. Cases where a signal could be found on the test line were evaluated as "+". Each signal was evaluated as "2+", "3+", "4+", or "5+", in that order, as the signal intensity increased (Table 2 shows the results).

As a result, it was found that high signal intensity can be observed in sample processing methods using a surfactant whose carbon number in the linear chain of the alkyl group is not less than 16.

TABLE 1

List of surfactants used

| No. | Type of surfactant | Alkyl group carbon number | POE polymerization degree |
|---|---|---|---|
| 1 | Polyoxyethylene oleyl ether | 18 (Linear, unsaturated fatty acid) | 15 |
| 2 | Polyoxyethylene stearyl ether | 18 (Linear, saturated fatty acid) | 20 |
| 3 | Polyoxyethylene cetyl ether | 16 (Linear, saturated fatty acid) | 13 |
| 4 | Polyoxyethylene octyl phenyl ether | 14 (6 out of 14 are cyclic) | 9 to 10 |
| 5 | Polyoxyethylene lauryl ether | 12 (Linear, saturated fatty acid) | 23 |
| 6 | n-Nonanoyl-N-methyl-D-glucamine | 8 (Linear, saturated fatty acid) | |
| 7 | n-Octanoyl-N-methyl-D-glucamine | 9 (Linear, saturated fatty acid) | |

TABLE 2

Differences in Signal Intensity among Surfactants

| No. | Type of surfactant | Signal intensity |
|---|---|---|
| | Detection of influenza A virus | |
| 1 | Polyoxyethylene oleyl ether | 3+ |
| 2 | Polyoxyethylene stearyl ether | 4+ |
| 3 | Polyoxyethylene cetyl ether | 5+ |
| 4 | Polyoxyethylene octyl phenyl ether | + |
| 5 | Polyoxyethylene lauryl ether | + |
| 6 | n-Nonanoyl-N-methyl-D-glucamine | + |
| 7 | n-Octanoyl-N-methyl-D-glucamine | + |
| | Detection of influenza B virus | |
| 2 | Polyoxyethylene stearyl ether | 3+ |
| 3 | Polyoxyethylene cetyl ether | 4+ |
| 4 | Polyoxyethylene octyl phenyl ether | + |

Example 2. Concentration of Polyoxyethylene Cetyl Ether Used

The influence of the concentration of polyoxyethylene cetyl ether on the immunochromatography for detection of influenza A or B virus M1 protein was investigated. Sample processing liquids each containing polyoxyethylene cetyl ether at a concentration shown in Table 3-1, and also containing 10 mM MES (pH 6.5) and 3% BSA as other components, were prepared. As a control, a sample which does not contain polyoxyethylene cetyl ether was provided (No. 1 in Table 3-1 and Table 3-2).

Subsequently, 30 μL of inactivated influenza A virus or inactivated influenza B virus was added to 400 μL of each of the sample processing liquids prepared, and each resulting mixture was mixed. To the sample pad portion of the influenza A or B virus test piece, 50 μL of the mixture was added dropwise, and visual judgment was carried out 10 minutes later. Cases where a signal could be found on the test line were evaluated as "+". The signal was evaluated as "2+", "3+", "4+", or "5+", in that order, as the signal intensity increased (the results are described in Table 2). "±" indicates that a weak signal was found.

As a result, for both type A and type B, signals stronger than that for the control condition (No. 1) could be found at polyoxyethylene cetyl ether concentrations within the range of 0.005 to 8 (w/v) %.

TABLE 3-1

Concentration of polyoxyethylene cetyl ether used (detection of influenza A virus)

| No. | Polyoxyethylene cetyl ether concentration {%(w/v)} | Signal intensity |
|---|---|---|
| 1 | 0 | ± |
| 2 | 0.001 | + |
| 3 | 0.005 | 3.0+ |
| 4 | 0.01 | 3.5+ |
| 5 | 0.05 | 4.5+ |
| 6 | 0.1 | 4.75+ |
| 7 | 0.5 | 4.75+ |
| 8 | 1 | 5+ |
| 9 | 2 | 5+ |
| 10 | 4 | 5+ |
| 11 | 8 | 5+ |

TABLE 3-2

Concentration of polyoxyethylene cetyl ether used (detection of influenza B virus)

| No. | Polyoxyethylene cetyl ether concentration {%(w/v)} | Signal intensity |
|---|---|---|
| 1 | 0 | ± |
| 2 | 0.001 | + |
| 3 | 0.005 | 1.5+ |
| 4 | 0.01 | 2+ |
| 5 | 0.05 | 2.5+ |
| 6 | 0.1 | 2.5+ |
| 7 | 0.5 | 3+ |
| 8 | 1 | 4+ |
| 9 | 2 | 4+ |

TABLE 3-2-continued

| Concentration of polyoxyethylene cetyl ether used (detection of influenza B virus) | | |
|---|---|---|
| No. | Polyoxyethylene cetyl ether concentration {%(w/v)} | Signal intensity |
| 10 | 4 | 4+ |
| 11 | 8 | 4+ |

Example 3. Effect of Addition of Chloride

The effects of addition of salt components on the immunochromatography for detection of influenza A or B virus M1 protein were investigated. First, sample processing liquids each containing 1 (w/v) % polyoxyethylene cetyl ether, one of sodium chloride, potassium chloride, and lithium chloride as a salt component at a concentration shown in Table 7, and 10 mM MES (pH 7.0) and 3% BSA as other components, were prepared. For control conditions, sample processing liquids which are the same as those described above except that salts are not contained were also prepared. Subsequently, 30 μL of inactivated influenza A virus or inactivated influenza B virus was added to 400 μL of each of the sample processing liquids prepared, and each resulting mixture was mixed. To the sample pad portion of the influenza B virus test piece, 50 μL of the mixture was added dropwise, and visual judgment was carried out 10 minutes later. Cases where a signal could be found on the test line were evaluated as "+". The signal intensity is expressed using a relative value such as "2+", "3+", "4+", or "5+", wherein the value increases as the signal intensity increases (Table 4-1 to Table 4-3 show results on type A, and Table 5-1 to Table 5-3 show results on type B).

As a result, slight increases in the signal intensity could be observed in the cases where a sample processing liquid supplemented with a chloride was used. In the cases of potassium chloride or lithium chloride, further slight increases in the signal intensity could be observed relative to other chlorides. It was found that a further increase in the signal intensity can be achieved with a sample processing liquid containing a mixture of potassium chloride and lithium chloride (No. 7 in Table 7) compared to cases where these are used individually. Although data are not shown, use of sodium thiocyanate caused non-specific reaction in some cases. It was therefore suggested that the type of the salt is important.

From the above results, it was discovered that the signal intensity in the immunochromatography for detection of M1 can be increased by adding a salt such as sodium chloride, potassium chloride, or lithium chloride, and using the salt at a concentration of 0.05 M to 1.5 M.

Table 4. Effect of Addition of Salt on Detection of Influenza A Virus

TABLE 4-1

| Addition of sodium chloride | | |
|---|---|---|
| No. | LiCl concentration (M) | Signal intensity |
| 1 | 0 | 5+ |
| 2 | 0.01 | 5.5+ |
| 3 | 0.05 | 5.75+ |
| 4 | 0.1 | 6+ |
| 5 | 0.3 | 6+ |
| 6 | 0.5 | 6+ |
| 7 | 1 | 6+ |
| 8 | 1.5 | 5.75+ |

TABLE 4-2

| Addition of potassium chloride | | |
|---|---|---|
| No. | KCl concentration (M) | Signal intensity |
| 1 | 0 | 5+ |
| 2 | 0.01 | 5.5+ |
| 3 | 0.05 | 5.75+ |
| 4 | 0.1 | 6+ |
| 5 | 0.3 | 6+ |
| 6 | 0.5 | 6+ |
| 7 | 1 | 6+ |
| 8 | 1.5 | 5.75+ |

TABLE 4-3

| Addition of lithium chloride | | |
|---|---|---|
| No. | LiCl concentration (M) | Signal intensity |
| 1 | 0 | 5+ |
| 2 | 0.01 | 5.5+ |
| 3 | 0.05 | 5.75+ |
| 4 | 0.1 | 6+ |
| 5 | 0.3 | 6+ |
| 6 | 0.5 | 6+ |
| 7 | 1 | 6+ |
| 8 | 1.5 | 5.75+ |

Table 5. Effect of Addition of Salt on Detection of Influenza B Virus

TABLE 5-1

| Addition of sodium chloride | | |
|---|---|---|
| No. | NaCl concentration (M) | Signal intensity |
| 1 | 0 | 4+ |
| 2 | 0.01 | 4+ |
| 3 | 0.05 | 4.25+ |
| 4 | 0.1 | 4.5+ |
| 5 | 0.3 | 4.5+ |
| 6 | 0.5 | 4.5+ |
| 7 | 1 | 4.5+ |
| 8 | 1.5 | 4.25+ |

TABLE 5-2

| Addition of potassium chloride | | |
|---|---|---|
| No. | KCl concentration (M) | Signal intensity |
| 1 | 0 | 4+ |
| 2 | 0.01 | 4+ |
| 3 | 0.05 | 4.25+ |
| 4 | 0.1 | 4.5+ |

TABLE 5-2-continued

| Addition of potassium chloride | | |
|---|---|---|
| No. | KCl concentration (M) | Signal intensity |
| 5 | 0.3 | 4.5+ |
| 6 | 0.5 | 4.5+ |
| 7 | 1 | 4.5+ |
| 8 | 1.5 | 4.25+ |

TABLE 5-3

| Addition of lithium chloride | | |
|---|---|---|
| No. | LiCl concentration (M) | Signal intensity |
| 1 | 0 | 4+ |
| 2 | 0.01 | 4+ |
| 3 | 0.05 | 4.25+ |
| 4 | 0.1 | 4.5+ |
| 5 | 0.3 | 4.5+ |
| 6 | 0.5 | 4.5+ |
| 7 | 1 | 4.5+ |
| 8 | 1.5 | 4.25+ |

Example 4. Study on Sensitivity-Increasing Effect of Sample Processing Method for M1 Detection Using Optimal Combination of Surfactant and Salt in Immunochromatography for Detection of Influenza A or B Virus M1

As the sample processing liquid for detection of M1, a sample processing liquid containing 2% polyoxyethylene cetyl ether and 1% polyoxyethylene octyl phenyl ether, and also containing 0.25 M potassium chloride and 0.25 M lithium chloride as salt components, and 10 mM MES (pH 7.0) and 3% BSA as other components, was prepared. To provide a control condition, a sample processing method containing 10 mM MES (pH 7.0), 3% BSA, and 1% polyoxyethylene octyl phenyl ether was prepared. The two kinds of sample processing methods described above were subjected to performance tests by immunochromatography using a dilution series (undiluted liquid, and up to 1024-fold dilutions) of influenza A or B virus. At the same time, comparison with conventional immunochromatography for detection of NP was carried out.

As a result, in the detection of influenza A virus, detection of the diluted sample prepared by 1024-fold dilution of the undiluted inactivated influenza A virus liquid was possible with the sample processing liquid for detection of M1, while detection of only the undiluted inactivated influenza A virus liquid was possible with the control sample processing liquid (Table 6-1). In the Table, the following symbols are used for representing the judgment results: "+", a signal could be found on the test line; "±", the reaction could be found although the signal was weak; "−", no signal could be found.

In the detection of influenza B virus, detection of the diluted sample prepared by 512-fold dilution of the undiluted inactivated influenza B virus liquid was possible with the sample processing liquid for detection of M1, while detection of only the undiluted inactivated influenza B virus liquid was possible with the control sample processing liquid, similarly to the cases of type A (Table 6-2).

In the immunochromatography for detection of M1 protein, not less than two times higher sensitivity could be observed for each of influenza A and B viruses compared to conventional immunochromatography for detection of NP (Table 6-1, Table 6-2).

From the above results, it was discovered that, as a sample processing method in immunochromatography for detection of influenza virus M1 protein, a sample processing method containing, as a surfactant component, a surfactant having a palmityl group, stearyl group, or oleyl group, and containing, as a salt component, potassium chloride, lithium chloride, or sodium chloride, is effective.

Table 6. Study on Sensitivity-Increasing Effect of Sample Processing Method for M1 Detection Using Optimal Combination of Surfactant and Salt in Immunochromatography for Detection of Influenza A or B Virus M1

TABLE 6-1

| Results of detection of influenza A virus using sample processing method for detection of M1 | | | |
|---|---|---|---|
| Dilution rate of influenza A virus | Control | Sample processing method for detection of M1 | Conventional NP detection system |
| Undiluted liquid | + | + | + |
| 2-fold | − | + | + |
| 16-fold | − | + | + |
| 64-fold | − | + | + |
| 128-fold | − | + | + |
| 256-fold | − | + | + |
| 512-fold | − | + | − |
| 1024-fold | − | ± | − |

TABLE 6-2

| Results of detection of influenza B virus using sample processing method for detection of M1 | | | |
|---|---|---|---|
| Dilution rate of influenza B virus | Control | Sample suspension for detection of M1 | Conventional NP detection system |
| Undiluted liquid | + | + | + |
| 2-fold | − | + | + |
| 16-fold | − | + | + |
| 64-fold | − | + | + |
| 128-fold | − | + | + |
| 256-fold | − | + | − |
| 512-fold | − | ± | − |
| 1024-fold | − | − | − |

The invention claimed is:

1. A sample processing method for an immunoassay for influenza virus matrix 1 protein, said sample processing method comprising:

bringing a sample containing influenza virus matrix 1 protein into contact with a sample processing liquid containing:

a surfactant comprising polyoxyethylene cetyl ether, and an alkali metal chloride with the final concentration of said chloride in said sample processing liquid being 0.3 to 1 M to produce a processed sample, said immunoassay for influenza virus matrix 1 protein including:

contacting the processed sample including influenza virus matrix 1 protein with an antibody or antigen binding fragment thereof which specifically binds influenza virus matrix 1 protein, said contacting being carried out in the presence of the surfactant added during the sample processing method.

2. The method according to claim 1, wherein the final concentration of said surfactant in said sample processing liquid is 0.005 (w/v) % to 8 (w/v) %.

3. The method according to claim 2, wherein said final concentration of surfactant in said sample processing liquid is 0.5 (w/v) % to 4 (w/v) %.

* * * * *